United States Patent [19]

Connick, Jr.

[11] 4,401,456

[45] Aug. 30, 1983

[54] CONTROLLED RELEASE OF BIOACTIVE MATERIALS USING ALGINATE GEL BEADS

[75] Inventor: William J. Connick, Jr., New Orleans, La.

[73] Assignee: The United States of America as represented by the Secretary of Agriculture, Washington, D.C.

[21] Appl. No.: 258,489

[22] Filed: Apr. 28, 1981

Related U.S. Application Data

[63] Continuation-in-part of Ser. No. 110,865, Jan. 9, 1980, abandoned.

[51] Int. Cl.³ .................... A01N 43/00; A01N 25/34
[52] U.S. Cl. .......................... 71/88; 71/65; 71/66; 71/67; 71/79; 71/93; 71/100; 71/115; 71/117; 71/118; 71/DIG. 1; 424/19; 424/304; 424/361
[58] Field of Search ............... 71/DIG. 1, 66, 88, 118, 71/117; 424/361, 304, 19

[56] References Cited

U.S. PATENT DOCUMENTS

| | | | |
|---|---|---|---|
| 2,441,729 | 5/1948 | Steiner | 424/361 |
| 2,635,067 | 4/1953 | Steiner et al. | 424/361 |
| 3,328,256 | 6/1967 | Gaunt | 71/DIG. 1 |
| 3,376,127 | 4/1968 | McConnell et al. | 71/66 |
| 3,516,846 | 6/1970 | Matson | 252/316 |
| 3,640,741 | 2/1972 | Etes | 424/361 |
| 3,649,239 | 3/1972 | Mitchell | 71/23 |
| 3,761,238 | 9/1973 | Errede | 71/66 |
| 4,053,627 | 10/1977 | Scher | 424/361 |
| 4,107,292 | 8/1978 | Nemeth | 424/361 |
| 4,242,357 | 12/1980 | Fuchs et al. | 424/304 |
| 4,370,160 | 1/1983 | Ziemelis | 71/DIG. 1 |

OTHER PUBLICATIONS

Fuji, "Multiwall Capsules," (1971), CA 75, No. 77838k, (1971).

Primary Examiner—Glennon H. Hollrah
Attorney, Agent, or Firm—M. Howard Silverstein; David G. McConnell; Raymond C. Von Bodungen

[57] ABSTRACT

Alginate gel beads containing bioactive materials dispersed therein are the product and the process of this invention. These beads can be made to either float or sink in aqueous environments, and are capable of providing the controlled release of their bioactive materials when applied to terrestrial or aqueous environments.

11 Claims, No Drawings

CONTROLLED RELEASE OF BIOACTIVE MATERIALS USING ALGINATE GEL BEADS

CROSS REFERENCE

This is a continuation-in-part of Ser. No. 110,865, filed Jan. 9, 1980 now abandoned.

BACKGROUND OF THE INVENTION (1) Field of the Invention

This invention relates to a means of providing controlled release of bioactive materials. More particularly, this invention relates to the preparation of alginate gel beads that contain a bioactive material dispersed therein.

(2) Description of the Prior Art

U.S. Pat. No. 4,053,627 describes the use of alginate gel discs to release juvenile hormone into an aqueous environment and U.S. Pat. No. 2,441,729 teaches the use of alginate gels as insecticidal jellies. These processes require that the salt which yields the gellant cation, such as calcium, be insoluble or almost insoluble in water, and be admixed with the alginate before adding to water. The salt must not, of itself, yield sufficient cations to gelatinize the alginic component quickly. It is a disadvantage of these processes that gel formation is relatively slow requiring about 10 minutes to 2 hours, during which time the mixture must be kept in a mold to hold the desired shape until gelation occurs.

U.S. Pat. No. 3,328,256 teaches the use of spherical beads for the controlled release of medicaments for use in the medical field. There are several disadvantages with the teachings of this particular process. In the preparation of the spherical beads, the patent speaks of using organic solvents which may be flammable or toxic and the products are entirely foreign to any use in agriculture.

U.S. Pat. No. 3,376,127 teaches the use of a herbicide which is applied to a carrier that is lighter than water as a means for attacking floating plants. No mention of controlled release is made; furthermore, any teaching for the use of floating means is accomplished by addition of solid lighter-than-water materials, or by using organic emulsions.

U.S. Pat. No. 4,107,292 teaches the use of xanthan gum added to formulations containing already existing polymer beads that contain insecticide in order to produce a better suspension of the polymer beads in water. The teaching is solely one of suspending an existing material in a liquid, to avoid settling in the container before spray application.

U.S. Pat. No. 3,649,239 and British Pat. No. 1,271,575 describe fertilizer compositions in alginate carriers that are applied to soil as liquid if the soil is acidic, and as gels if the soil is highly alkaline. In the latter case the gels are made by incorporating an acid gellant as an ingredient in the alginate fertilizer solution. It is a disadvantage that metal ions such as calcium are used only in certain circumstances as a soil application after the fertilizer composition has been applied to the soil.

British Pat. No. 1,236,885 teaches that alginates are useful in preparing multiwall capsules. A serious disadvantage in this process is that multiple process repetitions are required to achieve the necessary result. Furthermore, there is no teaching as to controlled release.

SUMMARY OF THE INVENTION

A process is provided for the preparation of alginate gel beads that contain bioactive materials dispersed therein. The beads prepared by the process of this invention are useful in providing controlled release of bioactive materials contained therein, when applied to aqueous and certain terrestrial environments. The beads of this invention can be prepared in a manner which will either cause the beads to sink or to float in an aqueous environment.

U.S. Pat. Nos. 4,053,627 and 2,441,729 teach away from the use of water soluble and highly ionized salts such as calcium chloride to prepare alginate gels.

In contrast, the process of the instant invention employs a solution of a soluble salt having a high concentration of gellant cations that are available for immediate reaction with the alginate. Said cation solution is separate and apart from the alginate until the moment of bead formation. Surprisingly, the formation of unique alginate beads containing bioactive materials occurs almost instantaneously according to the process of the present invention and a gel mold is not required.

U.S. Pat. No. 3,649,239 and British Pat. No. 1,271,575, unlike the instant invention, do not contemplate the use of herbicides or insecticides, cannot be applied to an aqueous environment, nor can they be used to prepare alginate beads. The instant invention differs drastically from U.S. Pat. No. 3,328,256 in at least three specific ways; (1) the reference patent is silent as to alginates, (2) the reference patent requires organic solvent in their bead preparation, (3) the beads of the reference patent are not formed by any chemically reactive means. U.S. Pat. Nos. 3,376,127 and 4,107,292, in contrast to the instant invention, do not use alginates as a herbicide carrier, do not use entrapped air for flotation, and do not envision controlled-release properties. British Pat. No. 1,236,885 teaches away from single-wall capsules or those with a uniform cross-section, and does not anticipate the use of herbicides or insecticides, drying the capsules, or controlled-release properties.

In the instant invention, a water-soluble salt of alginic acid and a bioactive material are mixed in water along with any desired adjuvants, and the mixture is then added dropwise into an aqueous solution of a di- or trivalent metal salt (called the gellant solution) that will cause the alginate to form a gel. As each drop comes in contact with the metal salt solution, almost immediately the gelation is initiated and a bead forms.

The floating beads of this invention are basically the same as the sinking beads except that a quantity of air is dispersed into the alginate/bioactive material/water mixture before droplets of this mixture are gelled, trapping air bubbles in the beads. The air provides buoyancy and the beads float in an aqueous environment. It was entirely unexpected and without mention in the prior art that air bubbles could be firmly entrapped in and cause the flotation of alginate gels.

Bioactive materials that contain the carboxy/carboxylate group may in some instances react with the cations of the gellant solution altering the solubility of the bioactive materials, thus providing an additional measure of control over their rate of release from the alginate gel beads.

DESCRIPTION OF THE PREFERRED EMBODIMENTS

The simplicity of the requirements for carying out the process of the present invention permits such latitude in design of equipment. A suitable apparatus, described only for the purpose of illustration and not to be construed as limiting the invention, consists of a reservoir to contain the alginate/bioactive material/water mixture that is equipped with a stopcock or similar device that allows the dropwise addition of the mixture through an orifice, the droplets falling through air a certain distance and impacting in the gellant solution. The gellant solution may be contained in any convenient vessel.

After a suitable time in the gellant solution, the resulting gel beads are removed by any suitable means such as filtration, screening, or straining. They may be rinsed in plain water if desired.

The beads can be used in this fully hydrated state or dried to any desired moisture content without losing their effectiveness. Small, hard granules result when the beads are dried.

Rate of addition of the mixture from the reservoir is a function of orifice size and the number of orifices used, and can be increased by applying air or piston pressure. Distance from the orifice to the surface of the gellant solution can be 0.1 to 15 ft or more but needs only to be far enough to allow the droplet to penetrate the surface of the gellant solution.

Size of the alginate gel beads depends upon the viscosity of the alginate/bioactive material/water mixture, the amount of water retained in the beads, and orifice size. An orifice of 0.1-5 mm in diameter is suitable, but the preferred range is 0.8-2 mm. Beads will be generally spherical or ellipsoidal with an average diameter of 0.1-6 mm. Smaller beads may be prepared by spraying the alginate/bioactive material/water mixture into the gellant bath.

A continuous process is possible. It requires continuous removal of gel beads and maintenance of the gellant concentration. It is also possible to extrude the alginate/bioactive material/water mixture into the gellant to form a string-like gel which can be cut into various lengths or dried and ground into granules.

Hydrated (undried) beads, if notimmediately used, are usually stored in an air tight jar. The well-known phenomenon of syneresis can occur with alginate gels as well as with many other polysaccharide gels. It is the loss of fluid from the gel caused by contraction. Most of the fluid loss occurs within the 24 hour period after preparation, but it can continue for a few weeks before coming to equilibrium. Some factors that infuence the amount of syneresis are algin composition, temperature, gellant, auxilliary chemicals, pH, and the chemical nature of the bioactive material. Usually the fluid that is ended is principally water and only a relatively small amount of bioactive material is lost. This liquid can be drained away from the gel beads or allowed to remain. Depending on the particular formulation, 0-80% by weight fluid loss from the beads can occur through syneresis. Dried beads do not exhibit syneresis.

The alginates used in the invention are any water soluble salts of alginic acid. These include sodium, potassium, magnesium, and ammonium alginate, and the alginates of organic bases such as amines. Sodium alginate is preferred. Viscosity of the alginate may vary widely but will influence gel strength to some degree. Highly refined alginates are not required for the practice of this invention.

An especially preferred alginate is the alginic acid, sodium salt, AX0450, available from MCB Manufacturing Chemists, Inc., Cincinnati, Ohio, having a bulk density of 43 lbs/cu ft, a pH of 7.2 in a 1% aqueous solution, and a viscosity (run with a Brookfield LVF @ 60 RPM) of 400 @ 1% and 3500 @ 2%.

Concentration of the alginate formulated in the initial alginate/bioactive material/water mixture is 0.5-3% by weight, but 1-1.5% is usually preferred.

The bioactive materials referred to in this invention are any materials that function as pesticides, herbicides, insecticides, algicides, bactericides, fungicides, biocides, nematicides, rodenticides, molluscicides, schistosomacides, insect pheromones, juvenile hormones, larvicides, adulticides, fertilizers, seed germination stimulants, plant growth regulators, and mixtures of these.

The bioactive materials may be in the form of liquids, solids, gases, emulsifiable concentrates, wettable powders, water soluble or insoluble materials, and combinations of these.

The excellent chemical compatibility of alginates allows admixture according to the present invention with a very wide choice of bioactive materials too numerous to list in their entirety. The following are only a few of these given for the purpose of illustration and should not be construed as limiting the scope of the invention. The common name is given first, followed by the chemical name.

molinate; S-ethyl hexahydro-1H-azepine-1-carbothioate alachlor; 2-chloro-2',6'-diethyl-N-(methoxymethyl)acetanilide butachlor; 2-chloro-2',6'-diethyl-N-(butoxymethyl)acetanilide vernolate; S-propyl dipropylthiocarbamate metribuzin; 4-amino-6-tert-butyl-3-(methylthio)-as-triazine-5(4H)-one decamethrin; 1-α-cyano-3-phenoxybenzyl d, cis dibromochrysanthemate 2,4-D; (2,4-dichlorophenoxy)acetic acid endothall; 7-oxabicyclo[2,2,1]heptane-2,3-dicarboxylic acid fenac;(2,3,6-trichlorophenyl)acetic acid Endothall, 2,4-D and fenac, along with many other bioactive materials, contain one or more carboxy/carboxylate groups in their structure. It is an important part of this invention that additional control over rate of release of these types of bioactive materials may be achieved. This occurs because of the dual role of the gellant solution whereby the gellant cations react not only with the alginate but can react with the carboxy/carboxylate group(s) of the bioactive material to form a free acid or salt form, altering its solubility in water and its rate of release from the alginate gel matrix. It is sometimes advantageous to use technical grade acid in these formulations.

Concentration of the bioactive material formulated in the alginate/bioactive material/water mixture can be as high as 50% by weight but is preferably in the range of 0.1-20%. The ingredients of this mixture may be incorporated in any order desired. The preferred pH range of the mixture is 4-12. The usual and preferred temperature of the mixture is 20°-30° C., but may be higher to reduce viscosity.

Cations that will gel alginate solutions are the cations of barium, lead, copper, strontium, cadmium, calcium, zinc, nickel, aluminum, acid ($H^+$), and mixtures of these. The gellant solution of the present invention consists of an aqueous solution of a soluble and ionized salt of a metal listed above, an acid, or a mixture of these. Choice of gellant will have an effect on gel properties and on the release rate of the bioactive material dispersed in the alginate gel bend. The preferred gellants are the chlorides and acetates of calcium, barium, and copper; the preferred acids are hydrochloric and acetic. Concentration of the metal salt or acid in the gellant solution may be up to 50% by weight, although 1–15% is preferred. Gelation proceeds faster as the concentration is increased. Reaction with sodium alginate and certain bioactive materials will reduce the effective concentration of gellant cations, therefore a sufficient concentration must be maintained to give the desired properties.

Temperature of the gellant solution can affect gel properties. It is an advantage of the present invention that heat does not have to be employed and most products can be made at 1°–30° C., but the preferred range is 20°–30° C. Heat sensitive bioactive material can be safely processed. However, any desired temperature up to and including the boiling point of the gellant solution may be used.

Reaction of the alginate/bioactive material/water mixture with the gellant solution is very rapid and produces a distinct gel bead immediately. Gelation proceeds from the outer surface to the center of the bead. Final gel properties such as hardness, strength, elasticity, size, durability, and release rate of the bioactive material are influenced by the time of residence in the gellant solution and should be optimized for each product. Generally, a residence time of 0.1–25 minutes may be used, but 1–10 minutes is usually sufficient.

The alginate gel beads can be made according to this invention so that they will float when applied to an aqueous environment. This is accomplished by stirring, agitating, or injecting air into the alginate/bioactive material/water mixture so that small air bubbles become dispersed throughout. Volume of the mixture may be increased several times thereby, but a 10–100% increase due to the air is usually sufficient. When droplets of the mixture are gelled, air bubbles are firmly entrapped in the beads making them buoyant.

The addition of certain materials to the alginate/bioactive material/water mixture may facilitate the incorporation of air and/or stabilize the new mixture. Adjuvants may be surfactants, gums, viscosity modifiers, and foam stabilizers. One suitable material cited for illustration only is Kelzan ®, a xanthum gum which is exocellular biopolysaccharide produced in a pure culture fermentation process by the microorganism *Xanthomonas campestris*. It is available from Kelco Co., Clark, N.J. Improved flotation of the beads is often obtained when 0.1–1% Kelzan ® is incorporated in the formulation.

As alternatives to the use of air, floating beads may be prepared by adding low density materials, other gases such as carbon dioxide or nitrogen, or blowing agents to the formulation. Gases, such as ethylenes, that have bioactive properties may also be used. The flotation properties of the beads made by the process of the present invention may sometimes be retained after drying.

In certain applications it may be desirable to add other ingredients to the alginate/bioactive material/water mixture, or to the gellant solution, or to the final gel beads. These additives may serve to alter the rate of release of the bioactive material, protect the gel beads from microbial attack, facilitate the preparation process, or reduce syneresis. They include solubilizing agents, biocides such as formaldehyde, enzymes, organic solvents, surfactants, viscosity modifiers, film-forming agents, natural and synthetic gums, sequestering agents, starch, talc, clay, fillers, fibers, and light-screening chemicals.

Controlled release refers to formulations or materials that dispense their active ingredients into the environment over a period of time. For the purpose of this invention, this time period can be short and measured in minutes or hours, or long and measured in days or even years. In the present invention, release of the bioactive material from the alginate beads occurs through processes such as leaching, diffusion, dissolution, and degradation. Just by virtue of the incorporation of a bioactive material in an alginate gel matrix a measure of controlled release is obtained. There may only be a small difference in release rate over that of conventional granular formulations when using very water-soluble materials, or significantly slower release when using relatively insoluble materials. Drying the gel beads usually gives products that have slower release rates than the hydrated material. In some instances, longer residence time in the gellant solution gives a slower release rate (as is readily shown in Table II). Rate of release in soil can be slowed by incorporating antimicrobial agents in the formulation to retard bead degradation by soil microbes.

The controlled release material can act as a carrier to place the active ingredient, a bioactive material in the present invention, near the target species. For example, and illustrating with controlled release herbicides: a sinking material can be applied to kill submerged aquatic weeds, a floating material can release herbicide in close proximity to floating aquatic weeds, and granules or beads can fall through foilage to release herbicides to the soil.

Controlled release materials may be used to reduce the number of applications neeed to perform a certain task, permit a lower concentration in the environment at any one time, and enhance effectiveness against the target species.

This invention is suitable for producing alginate gel beads containing bioactive material, said beads being useful for agricultural, industrial, and health-related purposes.

The following examples are provided to illustrate the invention and should not be construed as limiting the invention in any manner whatever.

EXAMPLE 1

To 6 grams of sodium alginate mixed with 25 grams of Ordram ® 8-E (a commercial formulation containing 90.9% molinate) was added 569 grams of water while stirring. A 60 gram portion of this mixture was added dropwise from a reservoir through glass tubes having a circular orifice of 1.3 mm diameter and falling a distance of 102 mm into 300 ml of 0.25 Molar $CaCl_2$ gellant solution contained in a 190 mm diameter vessel. The rate of addition was such that 5 minutes was required for the 60 g addition to take place. The alginate beads that had formed were allowed to remain in the gellant solution for 1 additional minute. The beads were then separated by filtration through a coarse frit, and stored in a closed jar. Liquid that exuded from the beads because of syneresis was periodically removed from the container. These beads would sink when added to water. (See Table I, Sample A.) When air-dried, the beads became hard granules that were less than 1 mm in diameter.

EXAMPLE 2

Alginate gel beads containing molinate were prepared as in Example 1 but using 0.25 M $BaCl_2$ as the gellant solution. (Refer to Table I, Sample B.)

EXAMPLE 3

Alginate gel beads containing molinate were prepared as in Example 1 but using 0.25 M $CuCl_2$ as the gellant solution. (Refer to Table I, Sample C.)

EXAMPLE 4

To 4 g of sodium alginate mixed with 27 g Machete ® (a commercial formulation containing 60% butachlor) was added 369 g water while stirring. The resulting mixture was processed as in Example 1 to produce alginate gel beads containing butachlor. (Refer to Table I, Sample D.)

The alginate gel beads of Examples 1-4 were soft, somewhat elastic, and resistant to rupture or fracture.

The products of Examples 1-4 were applied at a rate of 3 lbs/Acre, post emergence, into flooded pots containing rice infested with barnyardgrass. Greater than 80% control of the barnyardgrass was obtained after 1 week.

EXAMPLE 5

To 7.5 g of sodium alginate mixed with 33.3 g Lasso ® EC (a commercial formulation containing 45.1% alachlor) was added 459 g water while stirring. The resulting mixture was processed as in Example 1 to produce alginate gel beads containing alachlor. (Refer to Table I, Sample E.)

The product of Example 5 was applied preemergence to the soil at a rate of 2 lb/acre in outdoor test plots containing ragweed. The average of four replications gave 70% control of ragweed for the alginate gel bead product compared to 40% for a conventional application of the emulsifiable concentrate.

TABLE I
ALGINATE BEADS CONTAINING HERBICIDES

| Sample | Yield* at 2 weeks, % | % ai** | % Metal | Bead Diameter Avg., mm | Bead Weight, Avg., mg |
|---|---|---|---|---|---|
| MOLINATE | | | | | |
| A | 26 | 15.0 | 0.4 (Ca) | 2.1 | 4 |
| B | 38 | 10.7 | 0.7 (Ba) | 2.3 | 6 |
| C | 37 | 10.7 | 0.8 (Cu) | 2.4 | 7 |
| BUTACHLOR | | | | | |
| D | 28 | 14.0 | 0.4 (Ca) | 2.1 | 4 |
| ALACHLOR | | | | | |
| E | 31 | 9.6 | 0.6 (Ca) | 1.9 | 4 |

*% Yield = $\frac{\text{Product Weight}}{\text{Wt. of Mixture Dropped}} \times 100$
**Wt. % Active Ingredient of the Herbicide

EXAMPLE 6

A 1.5 g quantity of sodium alginate was added to the emulsion produced by combining 17.7 g of Decis ® EC 2-5 (a commercial product containing 25 g/l of decamethrin) and 80.8 g water. The resulting mixture was stirred at high speed in a homogenizer causing air to become dispersed throughout in the form of small bubbles.

A 38 g batch of the resulting mixture was processed as in Example 1 except that the drop height was 254 mm, the gellant solution was 0.25 M $BaCl_2$, and the residence time in the gellant was 5 additional minutes after addition was stopped.

The alginate gel beads that were produced contained 0.9% decamethrin, weighed an average of 6.5 mg, contained 2.2% Ba, and would float when added to water by virtue of the air bubbles entrapped therein.

When 5 of the beads were placed in a beaker containing 250 ml water and 25 mosquito larvae, the larvae were killed within 24 hours. The same beads were transferred to another beaker with larvae and again the larvae were killed within 24 hours. This procedure using the same beads was repeated again for a total of ten days with the same result demonstrating the controlled release of the insecticide.

The herbicides in Examples 7-14 contain one or more carboxy/carboxylate chemical group(s) in their structure.

EXAMPLE 7

To a solution of 101 g Ded Weed 40 ® (a commercial formulation containing 49.4% 2,4-D dimethylamine salt) in 391 g water was added 7.5 g of sodium alginate while stirring.

A 40 g batch of the resulting mixture was added dropwise from a reservoir through tubes having an orifice of 1.3 mm, and falling a distance of 102 mm into 400 ml of 0.25 M $BaCl_2$ gellant solution contained in a 175 mm dia. vessel. The rate of addition was such that the addition required 5 min. The alginate gel beads that had formed were allowed to remain in the gellant solution for 5 additional minutes, after which they were separated by filtration through a coarse frit, rinsed with water, and stored in a closed jar. Liquid that had exuded from the beads was periodically removed. The beads would sink when added to water. (Refer to Table II, Sample A.) Air drying produced hard granules. Calcium ions did not form gel beads using this formulation.

EXAMPLE 8

Alginate gel beads containing 2,4-D were prepared as in Example 7, except that the gellant solution was 0.25 M $BaCl_2$ that had been adjusted to pH 1 with hydrochloric acid. (Refer to Table II, Sample B.)

EXAMPLE 9

Alginate gel beads containing 2,4-D were prepared as in Example 8 except that the residence time in the gellant solution was 15-20 min. (Refer to Table II, Sample C.)

The alginate gel beads of Examples 7-9 were firm, spherical to ellipsoidal in shape, and resisted rupture or fracture. The data of Table II show the effect of residence time in the gellant solution and its pH on the rate of release of 2,4-D.

EXAMPLE 10

To 189 g of water was added 8 g of 2,4-D (ground to a powder) and 3 g of sodium alginate. After stirring for about 25 min. the resulting mixture (pH 4.0) was processed as in Example 7 to produce alginate gel beads containing solid particles of 2,4-D dispersed throughout.

EXAMPLE 11

Floating alginate gel beads were prepared as in Example 7 except for a drop height of 305 mm and a different procedure for making the alginate/2,4-D mixture: to a solution of 16.2 g Ded Weed 40 in 62.2 g water was added together 1.2 g sodium alginate and 0.4 g xanthum gum and the mixture stirred at sufficiently high speed to uniformly incorporate small air bubbles in such quantity that the volume of the mixture increased about 70%. The resulting beads contained 8% ae 2,4-D and weighed an average of 22 mg. Beads that were air-dried still retained much of their ability to float. Calcium ions did not form gel beads using this formulation.

Alginate gel beads prepared as in Examples 7–11 were added to water at a concentration of 1 ppm as 2,4-D acid, and caused 100% injury to the aquatic weed Eurasian watermilfoil by 8 weeks.

TABLE II

ALGINATE GEL BEADS CONTAINING 2,4-D

| Sample | Residence Time in Gellant Solution (min.) | Yield at 2 Weeks % | 2,4-D % Acid Equivalent | % Ba | Bead Diameter Avg., mm. | Bead Weight Avg., mg. | Release of* 2,4-D, 1-Day, % of Total |
|---|---|---|---|---|---|---|---|
| 0.25 M BaCl$_2$, A | pH = 5 5–10 | 97 | 8.5 | 2.4 | 3.5 | 10.6 | 94 |
| 0.25 M BaCl$_2$, B | pH = 1 5–10 | 59 | 14.0 | 0.7 | 2.5 | 6.1 | 81 |
| C | 15–20 | 57 | 14.5 | 0.6 | 2.6 | 6.3 | 64 |

*About 0.2 g Immersed 1-liter Deionized Water

EXAMPLE 12

To a solution of 99 g Aquathol$^R$K, a commercial herbicide formulation containing 40.3% endothall dipotassium salt, dissolved in 689 g water was added 12 g of sodium alginate while stirring. The resulting solution (pH 12) was added dropwise in 60 g batches through tubes having an orifice of 1.3 mm and falling a distance of 130 mm into 300 ml of 0.25 M CaCl$_2$ solution. Rate of addition was such that 60 g of the alginate-endothall solution was dropped in a 5 min period. The resulting gel beads were processed as in Example 7. (Refer to Table III, Sample A.)

At a 0.5 ml/l treatment rate, these beads caused 100% injury to Eurasian watermilfoil after 12 weeks exposure.

EXAMPLE 13

Alginate gal beads containing endothall were prepared as in Example 12 except that the gellant solution was 0.25 M BaCl$_2$. (Refer to Table III, Sample B.)

EXAMPLE 14

Alginate gel beads containing endothall were prepared as in Example 12 except that the gellant solution was 0.25 M CuCl$_2$. (Refer to Table III, Sample C.)

TABLE III

ALGINATE GEL BEADS CONTAINING ENDOTHALL

| Sample | Yield, 3 Weeks % | % Acid Equivalent, Endothall | % Metal | Bead Diameter, Avg., mm | Bead Weight Avg., mg. |
|---|---|---|---|---|---|
| A | 56 | 6.3 | 2.3 (Ca) | 3.0 | 17 |
| B | 95 | 3.8 | 3.0 (Ba) | 4.0 | 30 |
| C | 48 | 7.0 | 1.3 (Cu) | 2.7 | 15 |

I claim:
1. A process for preparing alginate gel beads containing a herbicide material consisting essentially of:
    (a) mixing a sufficient quantity of alginate for gelation with an effective quantity of herbicide material for incorporation in a final gel based, in water;
    (b) placing the mixture in a vessel equipped to dispense liquids dropwise;
    (c) mixing an effective quantity of water-soluble metal salt to gel mixture of (a), said salt selected from the group consisting of the chlorides of calcium, barium, and copper, with a sufficient quantity of water to obtain a solution;
    (d) adding, dropwise, the alginate mixture of (b) into the solution of (c); thus forming alginate gel beads which contain the herbicide material dispersed uniformly therein, allowing the beads to remain in contact with the solution of (c) for an effective period of time necessary to allow gelation; and
    (e) separating the gelled beads from the solution of (c).
2. The process of claim 1 wherein step (a) includes incorporating an effective quantity of air into the mixture to cause the resulting gelled beads to float when placed in an aqueous environment.
3. The process of claim 1 including a step of drying the beads of step (e).
4. The process of claim 1 wherein the herbicide is selected from the group consisting of:
    S-ethyl hexahydro-1H-azepine-1-carbothioate
    2-chloro-2',6'-diethyl-N-(methoxymethyl)acetanilide
    2-chloro-2',6'-diethyl-N-(butoxymethyl)acetanilide
    (2,4-dichlorophenoxy)acetic acid
    7-oxabicyclo[2,2,1]-heptane-2,3-dicarboxylic acid
5. The process of claim 1 wherein the alginate of (a) is sodium alginate.
6. The process of claim 5 wherein the mixture of (a) contains about from 1.0% to 1.5% by weight of alginate, and about from 3.0% to 10% by weight of herbicide material.
7. The process of claim 6 wherein the period of time allowed for the gelled beads to remain in contact with the solution in step (d) varies about from 5 to 20 minutes.
8. A process for preparing alginate gel beads containing an insecticide material consisting essentially of:
    (a) mixing an effective quantity of alginate for gelation with an effective quantity of insecticide material for incorporation in a final gel bead, in water;
    (b) placing the mixture in a vessel equipped to dispense liquids dropwise;
    (c) mixing an effective quantity of water soluble metal salt to gel the mixture of (a), said salt selected from the group consisting of the chlorides of calcium, barium, and copper, with an effective quantity of water to obtain a solution;
    (d) adding, dropwise, the alginate mixture of (b) into the solution of (c); thus forming alginate gel beads which contain the insecticide material dispersed uniformly therein, allowing the beads to remain in contact with the solution of (c) for an effective period of time necessary to allow gelation; and (e) separating the gelled beads from the solution of (c).

9. The process of claim 8 including incorporating a quantity of air into the mixture simultaneously with step (a).

10. The process of claim 9 including the additional step of drying the beads of step (e).

11. The process of claim 9 wherein the insecticide is 1-α-cyano-3-phenoxybenzyl d, cis dibromochrysanthemate.

* * * * *